US010759760B2

United States Patent
Martin et al.

(10) Patent No.: US 10,759,760 B2
(45) Date of Patent: Sep. 1, 2020

(54) PRECURSORS FOR RADIOFLUORINATION

(71) Applicant: ABX ADVANCED BIOCHEMICAL COMPOUNDS GMBH, Radeberg (DE)

(72) Inventors: René Martin, Dresden (DE); René Smits, Dresden (DE); Ronny Hesse, Dresden (DE); Alexander Hoepping, Dresden (DE); Marco Müller, Dresden (DE); Sandra Hübner, Heidenau (DE)

(73) Assignee: ABX ADVANCED BIOCHEMICAL COMPOUNDS GMBH, Radeberg (DE)

( * ) Notice: Subject to any disclaimer, the term of this patent is extended or adjusted under 35 U.S.C. 154(b) by 0 days.

(21) Appl. No.: 16/348,997

(22) PCT Filed: Nov. 17, 2017

(86) PCT No.: PCT/DE2017/100986
§ 371 (c)(1),
(2) Date: May 10, 2019

(87) PCT Pub. No.: WO2018/091043
PCT Pub. Date: May 24, 2018

(65) Prior Publication Data
US 2019/0263756 A1    Aug. 29, 2019

(30) Foreign Application Priority Data

Nov. 18, 2016 (DE) .................. 10 2016 122 273

(51) Int. Cl.
*C07D 213/82* (2006.01)
*C07B 59/00* (2006.01)
*A61K 51/04* (2006.01)

(52) U.S. Cl.
CPC .......... *C07D 213/82* (2013.01); *C07B 59/002* (2013.01); *A61K 51/0455* (2013.01); *C07B 2200/05* (2013.01)

(58) Field of Classification Search
None
See application file for complete search history.

(56) References Cited

FOREIGN PATENT DOCUMENTS

| WO | 2015/004029 A1 | 1/2015 |
| WO | 2016/030329 A1 | 3/2016 |
| WO | 2016/065145 A2 | 4/2016 |
| WO | 2017/054907 A1 | 4/2017 |

OTHER PUBLICATIONS

International Search Report dated Feb. 26, 2018 in corresponding International application No. PCT/DE2017/100986; 9 pages.
Ravert, et al., "An improved synthesis of the radiolabeled prostate-specific membrane antigen inhibitor, [18F] DCFPyL : Radiolabeled PSMA inhibitor, [18F] DCFPyL", Journal of Labelled Compounds and Radiopharmaceuticals, Sep. 1, 2016, p. 439-450, vol. 59, No. 11; 12 pages.
Kelly, et al., "Synthesis and pre-clinical evaluation of a new class of high-affinity 18F-labeled PSMA ligands for detection of prostate cancer by PET imaging", European Journal of Nuclear Medicine and Molecular Imaging, Nov. 15, 2016, p. 647-661, vol. 44, No. 4; 15 pages.
Chen, et al., "2-(3-{1-Carboxy-5-[(6-[18F]Fluoro-Pyridine-3-Carbonyl)-Amino]-Pentyl}-Ureido-Pentanedioic Acid, [18F]DCFPyL, a PSMA-Based PET Imaging Agent for Prostate Cancer", Clinical Cancer Research, Dec. 15, 2011, p. 7645-7653, vol. 17, No. 24; 10 pages.
Poethko, et al., "Two-step methodology for high-yield routine radiohalogenation of peptides: 18F-labeled RGD and octreotide analogs", The Journal of Nuclear Medicine, Society of Nuclear Medicine, May 1, 2004, p. 892-902, vol. 45, No. 5; 12 pages.
Cardinale, et al., "Preliminary Results on the Synthesis of 18F-PSMA-1007 by Direct One-Step Fluorination", Journal of Nuclear Medicine, May 1, 2017, vol. 58; 2 pages.
Bouvet, et al., "Automated synthesis of [18F]DCFPyL via direct radiofluorination and validation in preclinical prostate cancer models", EJNMMI Research 2016, p. 1-15; 15 pages.
International Preliminary Report on Patentability dated May 23, 2019 in corresponding International Application No. PCT/DE2017/100986; 8 pages.
Examination report No. 1 for your standard patent application dated May 26, 2020, in corresponding Australian Application No. 2017359864, 4 pages.
Examination Report dated Jan. 27, 2020 in corresponding European Application No. 17 811 189.4, 10 pages including partial machine-generated English-language translation.

*Primary Examiner* — Zinna Northington Davis
(74) *Attorney, Agent, or Firm* — Maier & Maier, PLLC

(57) ABSTRACT

A method for producing a radiofluorinated compound having an aromatic or heteroaromatic ring carrying [$^{18}$F] fluorine as first substituent, a bonding unit, which can bind to a peptide or peptide mimetic, and a spacer group connected via bond A$^1$ to the bonding unit and via bond A$^2$ to the ring, wherein the bonding unit has second substituent(s) —OH, —CONH, and/or —COOH. The steps include (a) providing a precursor having the ring carrying a substituent Y, bonding unit with the second substituent(s), and spacer group, wherein substituent Y is —N$^+$(R$^1$R$^2$R$^3$), —NO$_2$, —Cl, —Br, —F, or —I, and R$^1$, R$^2$, and R$^3$ are independently C$_1$-C$_6$ alkyl; and (b) reacting the precursor with a [$^{18}$F] fluoride anion in the presence of an activation salt to the radiofluorinated compound, which has a cation N$^+$(R$^4$R$^5$R$^6$R$^7$) with R$^4$, R$^5$, R$^6$, and R$^7$ being independently C$_1$-C$_6$ alkyl, wherein the substituent Y is replaced by [$^{18}$F] fluoride.

8 Claims, No Drawings

PRECURSORS FOR RADIOFLUORINATION

The invention relates to precursors for radiofluorination as well as methods for radiofluorination of said precursors.

BACKGROUND

In medical diagnostics there are used short-lived, radiolabeled compounds, so-called radiotracers, the physiological and biochemical properties of which allow a non-invasive tomographic detection of metabolic processes in the human body. By using the modern tomographic method of positron emission computer-assisted tomography (PET) metabolic processes can be quantified and the biodistribution of the radiodiagnostic agent can be detected from the outside by means of said radiotracers. The tomographic detection of radiotracers, such as e.g. 2-desoxy-2-[$^{18}$F]fluoro-D-glucose ([$^{18}$F]-FDG), allows an early diagnosis of tumors that significantly differ from each other in view of the glucose metabolism of normal tissue. By developing new radiotracers on the basis of pharmacologically interesting compounds new possibilities of non-invasive diagnostics of various clinical pictures have opened in recent years.

Global share of positron emission computer-assisted tomography (PET) of the total market of diagnosis by means of imaging methods in recent years has increased explosively. The largest share of this is accounted for by [$^{18}$F] fluoride as a radioactive probe, since in the form of the F-18 labeled sugar derivative ([$^{18}$F]-FDG) it visualizes the exact localization of tumors up to the millimeter range by means of PET and allows an exact localization of the tumor spread. However, it has been shown that [$^{18}$F]-FDG, that is often referred to as the "workhorse" of nuclear medicine, is only of limited use for the detection of primary, organ-restricted prostatic cancer (Bouvez et al., *EJNMMI Research* 2016, 6, 40). For this reason, for the detection of prostatic tumors and metastases that express PSMA (prostate-specific membrane antigen) to greater extent new radiotracers such as [$^{18}$F]-DCFPyL (Formula 1) and [$^{18}$F]F-PSMA-1007 (Formula 2) have been developed that can be used to detect the prostate-specific membrane antigens (PSMA).

Formula I

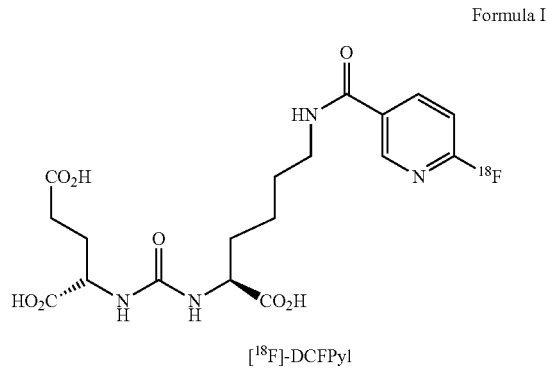

[$^{18}$F]-DCFPyl

Formula 2

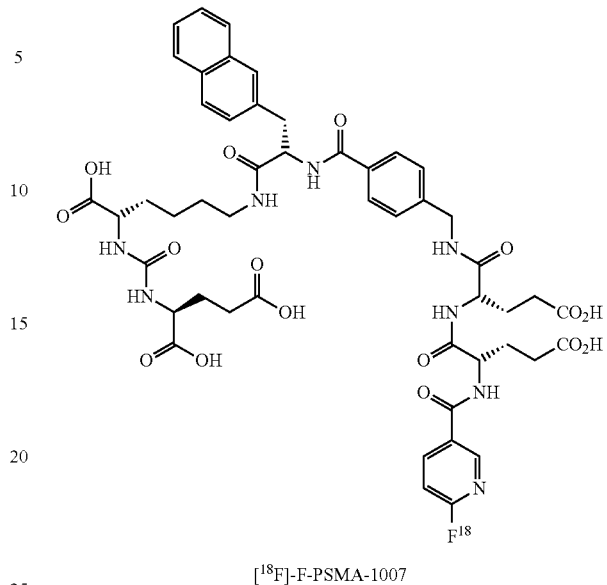

[$^{18}$F]-F-PSMA-1007

It can be seen in formulas 1 and 2 that said radiotracers are multifunctional molecules, because they have a large number of free functional groups such as e.g., —OH, —CONH, —COOH. Normally, molecules with many free functional groups are not suitable for direct labeling with $^{18}$F. The functional groups often react with the [$^{18}$F] fluoride anion, usually so that HF is generated. Thus, no reactive fluoride is available for a successful radiolabeling anymore. Moreover, the solubility of highly polar compounds in anhydrous solvents is greatly reduced. Moreover, in aqueous solvents the [$^{18}$F] fluoride anion is not sufficiently activated, therefore in radiochemistry use is made of so-called "naked anions" in which in organic solution the positive center of the counterion such as e.g., with tetra-n-butyl-ammonium salts is shielded by non-polar hydrocarbon chains.

Thus, state of the art with these multifunctional molecules is to insert protective groups or to insert prosthetic groups that have been radioactively labeled in advance (both two-stage reactions), so that only the synthetically introduced leaving group (in this case trimethylammonium triflate) can react with the tetra-n-butyl-ammonium hydrogen carbonate-activated [$^{18}$F] fluoride anion. These radiotracers for reasons of radiation protection are usually prepared in so-called "hot cells" with automated synthesis modules using disposable materials such as e.g., cassettes, in particular sterilized cassettes, and reagents. Expensive, multi-stage synthesis routes can often not be realized in a cost-effective way with these systems.

However, insertion of protective groups always is disadvantageous in that these have to be expensively deprotected by acids or bases. Thus, here we are also talking about 2-stage reactions: First stage: labeling with $^{18}$F. Second Stage: deprotection with acid or base. Both, using protective groups and acids and bases often leads to significant by-products that have to be separated from the desired $^{18}$F-labeled substance. This is usually accomplished with high equipment costs by means of a HPLC (high performance liquid chromatography) and therefore, is time-consuming and costly. Synthesis via prosthetic groups is also carried out over at least two stages. First, the prosthetic group is labeled with $^{18}$F, then it is coupled to the target molecule.

Time factor plays a significant role in radiopharmacy, since the $^{18}$fluoride anion has a half-life of only 109 minutes and thus, any prolongation in synthesis time and transportation route results in direct effects on the amount of the patient doses to be obtained.

Accordingly, two ways are known for the preparation of [18F]-DCFPyL: The first way is a two-stage synthesis by means of a protected precursor (Ravert et al., *J. Label Compd. Radiopharm* 2016, 59, 439-50; scheme 1, or Bouvet et al., *EJNMMI Research*, 2016, 6: 40, respectively).

The total yield on the ELIXYS microfluidic module is 19% on average after 87 min of synthesis.

The second way is a three-stage synthesis and runs via a prosthetic group (Chen et al., *Clin. Cancer Res.* 2011, 17, 7645-53; scheme 2)

Scheme 2

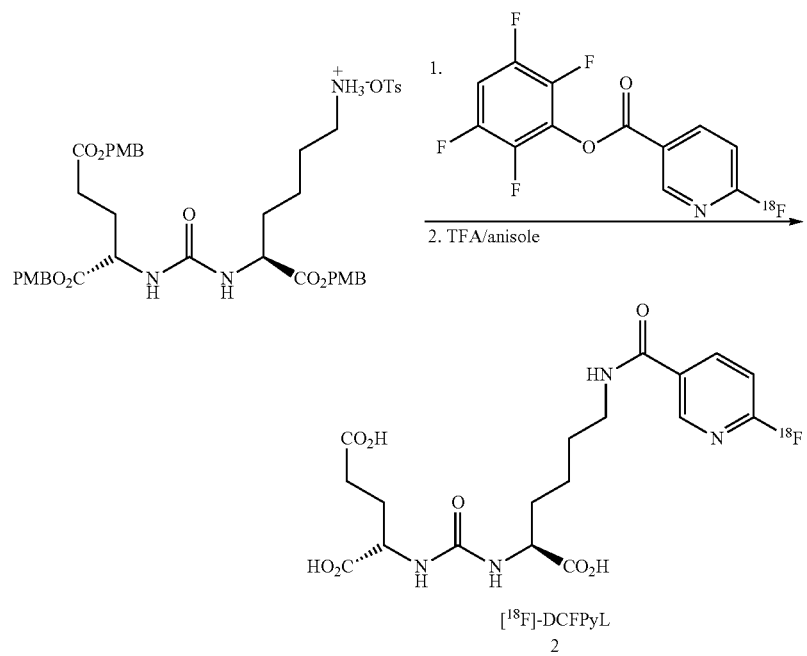

Here, in the first step the prosthetic group 6-[18F] fluoronicotinic acid-2,3,5,6-tetrafluorophenylester is prepared. In the second step the ammonium salt (1) is coupled to 6-[18F] fluoronicotinic acid-2,3,5,6-tetrafluorophenylester (a), and in the third step the PMB protective groups are removed with TFA and anisole (b). Thereby, [18F]F-DCFPyL (2) is obtained in a total yield of only 5 to 10%.

The method for radiofluorination of precursors described in WO 2015/004029 A1 requires converting carboxyl groups to carboxylate anions to form salts with cationic chelates or quaternary ammonium cations. Thus, in a chemical synthesis upstream the radiofluorination the precursors have to be converted into salts in the form of $K^+$/K222. The method particularly aims at the radiofluorination of free amino acids. Radiofluorination is carried out in the alkaline range. The radiochemical yields in no event exceed 26%.

Scheme 1

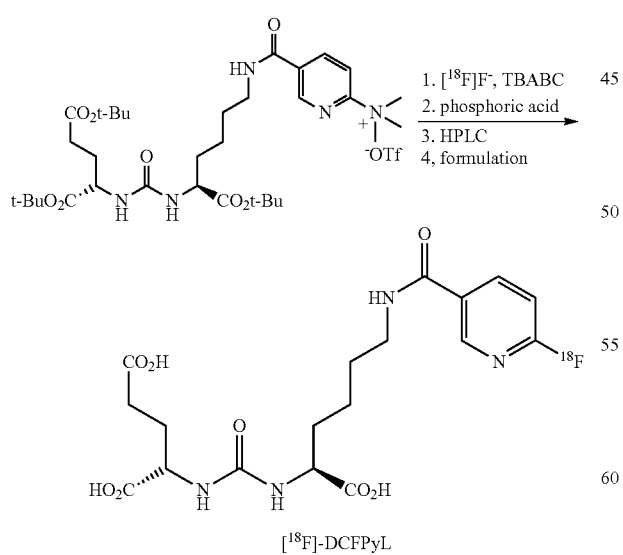

The carboxylic acid functionalities in the precursor are protected as tert-butylester. The end product is released with acid in the second step. Purification is carried out by HPLC.

SUMMARY

The problem underlying the invention is to eliminate the drawbacks according to the prior art. In particular, precursors are to be provided that allow a direct radiofluorination with high yields of radiotracers. Further, a method for radiofluorination of said precursors is to be provided.

This problem is solved by the invention. Suitable developments of the invention result from the features hereinafter.

According to the invention there is provided a method for producing a radiofluorinated compound, which has an aromatic or heteroaromatic ring, which carries [18F] fluorine as the first substituent, a bonding unit, which can bind to a peptide or a peptide mimetic, as well as a spacer group connecting the aromatic or heteroaromatic ring to the bonding unit. The bonding unit carries at least one second substituent selected from the group consisting of —OH, —CONH, and —COOH. The bonding unit is connected to the spacer group via a bond $A^1$. The spacer group is connected to the aromatic or heteroaromatic ring via a bond $A^2$. The method comprises the steps of:

DETAILED DESCRIPTION (a) providing a precursor, which has the aromatic or heteroaromatic ring, which carries a substituent Y, the bonding unit, which can bind to the peptide or peptide mimetic and carries at least one second substituent, as well as the spacer group, wherein Y is $—N^+(R^1R^2R^3)$, $—NO_2$, $—Cl$, $—Br$, $—F$, or $—I$, and $R^1$, $R^2$, and $R^3$ are the same or different from each other and each are unsubstituted or substituted $C_1$-$C_6$ alkyl; and (b) reacting the precursor with a [$^{18}$F] fluoride anion in the presence of an activation salt to the radiofluorinated compound, wherein the substituent Y is replaced by [$^{18}$F] fluoride, and wherein the activation salt has a cation of the general formula $N^+(R^4R^5R^6R^7)$, wherein $R^4$, $R^5$, $R^6$, and $R^7$ are the same or different from each other and each are unsubstituted or substituted $C_1$-$C_6$ alkyl.

According to the invention a complete automation of the reaction of the precursor with [$^{18}$F]fluoride anion in the presence of the activation salt to the radiofluorinated compound can be provided on a conventional synthesis module with subsequent cartridge purification. Here, the radiofluorinated compound can be obtained in radiochemical yields in excess of 40%.

The term "$C_1$-$C_6$ alkyl" relates to straight or branched, saturated, aliphatic hydrocarbon groups with 1 to 6 carbon atoms. Examples of $C_1$-$C_6$ alkyl groups are methyl, ethyl, n-propyl, iso-propyl, n-butyl, iso-butyl, sec-butyl, tert-butyl, n-pentyl, n-hexyl.

The term "substituted $C_1$-$C_6$ alkyl" relates to $C_1$-$C_6$ alkyl, as defined above, which has one or more substituents selected from the group consisting of $NH_2$, $NH(C_1$-$C_4$ alkyl), $N(C_1$-$C_4$ alkyl)$_2$, halogen, $C_1$-$C_4$ alkyl, OH, O($C_1$-$C_4$ alkyl), $NO_2$, CN, $CO_2H$ or $CO_2(C_1$-$C_4$ alkyl), wherein each of the preceding $C_1$-$C_4$ alkyl groups is unsubstituted or substituted with at least one halogen atom. The term "halogen" relates to fluorine, chlorine, bromine, and iodine.

In the present invention, the term precursor relates to a chemical compound that can be converted to a radiochemical compound, i.e. the radiofluorinated compound, by radiofluorination without using protective groups. The precursor has no carboxylate groups, in particular no carboxylate anions —COO$^-$. Thus, the precursor also has no carboxylate groups in the form of a salt with a cation, for example a cationic chelate or a quaternary ammonium cation.

However, the precursor can have one or more carboxyl groups —COOH. With the method according to the invention a precursor, which has one or more carboxyl groups, can be converted to a radiofluorinated compound without using protective groups. The precursor only differs from the radiofluorinated compound in that the substituent Y is replaced by [$^{18}$F]fluorine. Substituent Y of the precursor and the [$^{18}$F] fluorine substituent of the radiofluorinated compound are in the same position.

Preferably, substituent Y is $—N^+(R^1R^2R^3)$, wherein $R^1$, $R^2$, and $R^3$ are the same or different from each other and each are unsubstituted or substituted $C_1$-$C_6$ alkyl. Preferably, $R^1$, $R^2$, and $R^3$ are the same and are methyl or butyl, wherein methyl is particularly preferred. In this case, the group $—N^+(R^1R^2R^3)$, which carries the aromatic or heteroaromatic ring of the precursor, is a quaternary trimethylammonium group. The anion relating to the group $—N^+(R^1R^2R^3)$ of the precursor can be any anion. For example, the anion can be selected from the group comprising a fluorine, iodine, bromine, chlorine, sulphonate, sulphate, phosphate, alkylsulphate, arylsulphate, or carboxylate anion. Preferably, as the anion a carboxylate anion can be provided, for example $CF_3COO^-$, $CH_3COO^-$, $C_2H_5COO^-$, or $HCOO^-$.

If $R^1$, $R^2$, and $R^3$ in the group $—N^+(R^1R^2R^3)$ each are methyl, then it is preferred that the anion of the group $—N^+(R^1R^2R^3)$ is selected from the group consisting of trifluoroacetate ($CF_3COO^-$), acetate ($CH_3COO^-$), propionate ($C_2H_5COO^-$), or formate ($HCOO^-$).

The aromatic or heteroaromatic ring of the precursor and thus, of the radiochemical compound, is preferably a monocyclic ring or a fused ring system of two or more rings with a monocyclic ring being preferred. The heteroatom of a heteroaromatic ring is preferably selected from the group comprising N, O, and S. Preferably, the heteroatom is N. A heteroaromatic ring can have one or more heteroatoms. Preferably, the heteroaromatic ring has one or two heteroatoms, preferably one or two nitrogen atoms. In this case, the ring can be a pyridine ring, a pyridazine ring, a pyrimidine ring, or a pyrazine ring.

A preferred aromatic or heteroaromatic ring, which carries a substituent Y, is shown in the general formula VI:

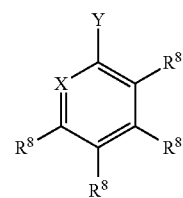

Formula VI wherein X is $C—R^8$ or N, Y is $—N^+(R^1R^2R^3)$, $—NO_2$, $—Cl$, $—Br$, $—F$, or $—I$, wherein $R^1$, $R^2$, and $R^3$ are defined as above and $R^8$ each independently is the bond $A^2$ to the spacer, hydrogen or unsubstituted or substituted $C_1$-$C_6$ alkyl, with the provision that exactly one residue $R^8$ is a bond $A^2$ to the spacer group and the remaining one of $R^8$ are the same or different from each other and each represent hydrogen or unsubstituted or substituted $C_1$-$C_6$ alkyl.

A particularly preferred aromatic or heteroaromatic ring has the group $—N^+(R^1R^2R^3)$ as substituent Y and bond $A^2$ in para position to the group $—N^+(R^1R^2R^3)$, as is shown in general formula VIa:

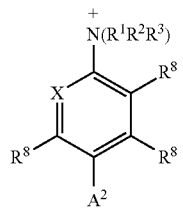

Formula VIa wherein X is $C—R^8$ or N, $R^1$, $R^2$, and $R^3$ are defined as above and $R^8$ each independently is hydrogen or unsubstituted or substituted $C_1$-$C_6$ alkyl.

A more preferred aromatic or heteroaromatic ring, which carries a group —N$^+$(R$^1$R$^2$R$^3$) as substituent Y, has bond A$^2$ in para position to group —N$^+$(R$^1$R$^2$R$^3$), as is shown in general formula VIb:

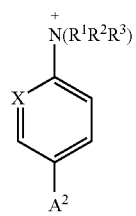

Formula VIb wherein X is C—R$^8$ or N, R$^1$, R$^2$, and R$^3$ are defined as above and R$^8$ is hydrogen or unsubstituted or substituted C$_1$-C$_6$ alkyl. Preferably, X is N and R$^1$, R$^2$, and R$^3$ are defined as above.

A particularly preferred embodiment of the aromatic or heteroaromatic ring, which carries a group —N$^+$(R$^1$R$^2$R$^3$) as substituent Y, is shown in formula VIc:

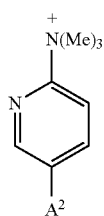

Formula VIc wherein Me represents methyl. In formula VIc, with respect to general formula VI, X is N; R$^1$, R$^2$, and R$^3$ are methyl; R$^8$ in para position to the —N$^+$(R$^1$R$^2$R$^3$) group is A$^2$, and the remaining R$^8$ are hydrogen.

A preferred aromatic or heteroaromatic ring, which carries a substituent Y, is shown in general formula VId:

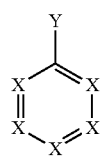

Formula VId wherein
  X each is C—R$^8$ or N, with the provision that at most two of the moieties X are N and the remaining ones of moieties X are C—R$^8$; and
  Y is —N$^+$(R$^1$R$^2$R$^3$), —NO$_2$, —Cl, —Br, —F, or —I, wherein R$^1$, R$^2$, and R$^3$ are as defined above and R$^8$ each independently is the bond A$^2$ to the spacer, hydrogen or unsubstituted or substituted C$_1$-C$_6$ alkyl, with the provision that exactly one of residues R$^8$ is a bond A$^2$ to the spacer group and the remaining ones of R$^8$ are the same or different from each other and each represent hydrogen or unsubstituted or substituted C$_1$-C$_6$ alkyl.

The bonding unit is able to bind to a peptide or to a peptide mimetic. For example, the radiochemical compound can specifically couple to a functional unit of the peptide or the peptide mimetic via the bonding unit. The bonding unit of the precursor and thus, the radiochemical compound may be a bonding unit of general formula I:

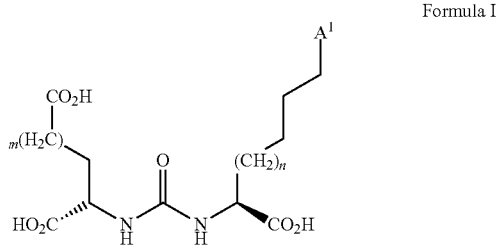

Formula I wherein A$^1$ is the bond via which the bonding unit is connected to the spacer group, and m and n are the same or different from each other and each are an integer of from 0 to 10. Thus, m and n each independently may be 0, 1, 2, 3, 4, 5, 6, 7, 8, 9, or 10. Preferably, m=1 and n=1. The bonding unit shown in formula I is able to bind to the protein PSMA (prostate-specific membrane antigen). PSMA is a protein that is expressed in the prostate of a mammal. With prostatic cancer it is expressed to a higher extent compared to a healthy prostate.

The spacer group of the precursor and thus, the radiochemical compound is preferably a spacer group of general formula II or general formula III:

Formula II

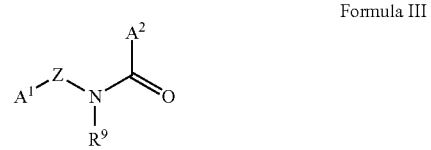

Formula III wherein A$^1$ is the bond via which the spacer group is connected to the bonding unit, A$^2$ is the bond via which the spacer group is connected to the aromatic or heteroaromatic ring of the precursor or the radiochemical compound, R$^9$ is hydrogen or an unsubstituted or substituted C$_1$-C$_6$ alkyl group, and Z is an unsubstituted or mono- or poly-substituted hydrocarbon. Preferably, R$^9$ is hydrogen.

In one embodiment of the invention Z is a group of formula VII:

Formula VII

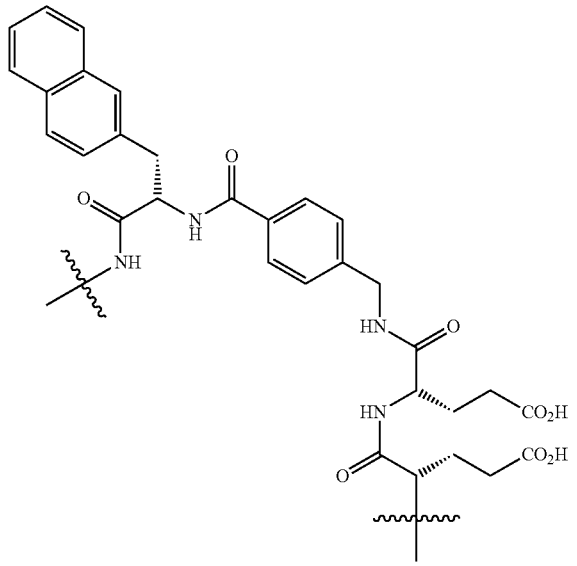

A spacer group of formula III the Z group of which has the meaning shown in formula VII is in formula IIIa:

Formula IIIa

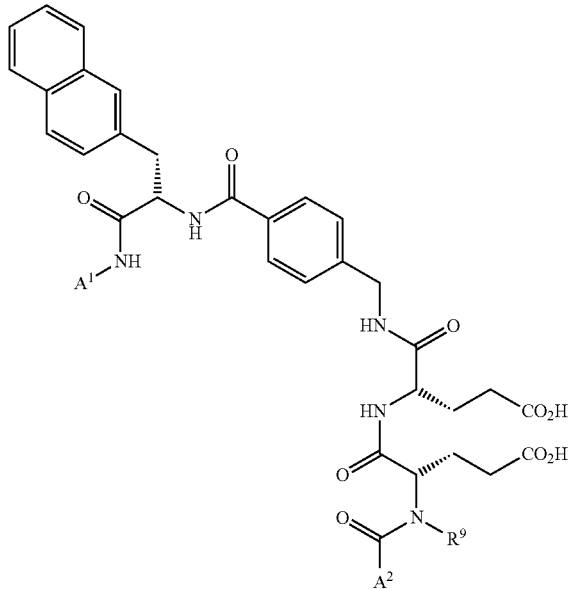

wherein $R^9$ is as defined above. Preferably, $R^9$ is hydrogen.

According to the invention, reacting the precursor is to be done with a [$^{18}$F] fluoride anion in the presence of an activation salt to the radiofluorinated compound. Here, the substituent Y is replaced by [$^{18}$F] fluoride. The activation salt is for activation of the [$^{18}$F] fluoride anion. The activation salt has a cation with the general formula $N^+(R^4R^5R^6R^7)$, wherein $R^4$, $R^5$, $R^6$, and $R^7$ are the same or different from each other and each are unsubstituted or substituted $C_1$-$C_6$ alkyl. It has been shown that such activation salts are suitable not only to react the described precursors to radiofluorinated compounds, but also for radiofluorination of other precursors. Preferably, $R^4$, $R^5$, $R^6$, and $R^7$ each are unsubstituted $C_1$-$C_6$ alkyl, more preferred propyl, butyl, or pentyl, especially preferred n-butyl each. Preferably, the activation salt has an anion selected from the group comprising hydrogen carbonate ($HCO_3^-$), hydrogen sulphate ($HSO_4^-$), oxalate, phosphate, and toluenesulphonate. Hydrogen carbonate and phosphate are more preferred. Phosphate is particularly preferred. The cation of general formula $N^+(R^4R^5R^6R^7)$ and the anion are present in the activation salt in a stoichiometric ratio. In a preferred embodiment, the activation salt is tetra-n-butyl-ammonium hydrogen carbonate or tetra-n-butyl-ammonium phosphate, wherein tetra-n-butyl-ammonium phosphate is particularly preferred. In the following, an activation salt having the tetra-n-butyl-ammonium cation is also referred to as TBA.

Using an activation salt having a cation of general formula $N^+(R^4R^5R^6R^7)$, wherein $R^4$, $R^5$, $R^6$, and $R^7$ are the same or different from each other and each are unsubstituted or substituted $C_1$-$C_6$ alkyl, and hydrogen sulphate, oxalate, phosphate, and toluenesulphonate as the anion, to activate [$^{18}$F] fluoride anions is unknown so far. These activation salts are not limited to the reaction of the described precursors to radiofluorinated compounds, but can also be used for radiofluorination of other precursors. Preferably, $R^4$, $R^5$, $R^6$, and $R^7$ in the hydrogen sulphate, oxalate, phosphate, and toluenesulphonate salt each are unsubstituted $C_1$-$C_6$ alkyl, more preferred propyl, butyl, or pentyl, particularly preferred n-butyl each. Hydrogen carbonate and phosphate salts are more preferred. Phosphate salt is particularly preferred. In a preferred embodiment the activation salt is tetra-n-butyl-ammonium hydrogen carbonate or tetra-n-butyl-ammonium phosphate, wherein tetra-n-butyl-ammonium phosphate is particularly preferred.

Preferably, the activation salt is in a polar solution, particularly preferred in a solution with water or a hydrous mixed solvent. The mixed solvent may be for example water containing an alcohol such as ethanol. The alcoholic additive is to stabilize the solution. The activation salt may be provided as a 0.001 to 0.1 M solution, in particular as a 0.075 M solution, for example.

The radiofluorinated compound is for example [$^{18}$F]-DCFPyL (see Formula 1, supra) or [$^{18}$F]F-PSMA-1007 (see formula 2, supra). A precursor that is preferred for the preparation of [$^{18}$F]-DCFPyL is a compound of general formula IV:

Formula IV

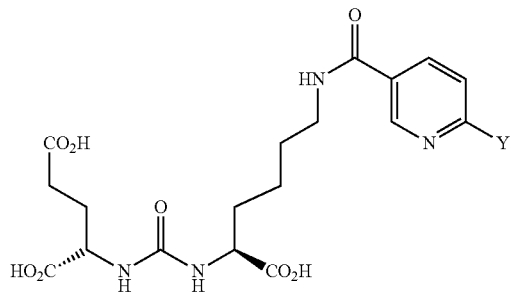

wherein substituent Y is selected from the group consisting of —$N^+(R^1R^2R^3)$, —$NO_2$, —Cl, —Br, —F, or —I, and $R^1$, $R^2$, and $R^3$ are the same or different from each other and each are unsubstituted or substituted $C_1$-$C_6$ alkyl. The bonding unit of the precursor shown in formula IV corresponds to the bonding unit shown in formula I, wherein m and n each are 1.

A precursor that is more preferred for the preparation of [$^{18}$F]-DCFPyL is a compound of general formula IVa:

Formula IVa

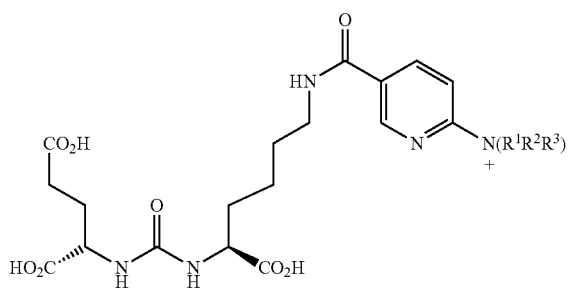

wherein $R^1$, $R^2$, and $R^3$ are the same or different from each other and each are unsubstituted or substituted $C_1$-$C_6$ alkyl. Particularly preferred $R^1$, $R^2$, and $R^3$ each are methyl. A precursor of formula IVa, in which $R^1$, $R^2$, and $R^3$ each are methyl, is illustrated in formula IVb.

Formula IVb

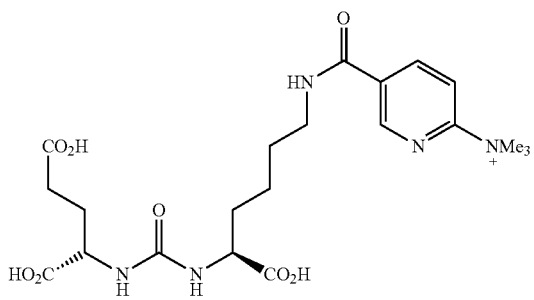

A precursor preferred for the preparation of [$^{18}$F]F-PSMA-1007 is a compound of general formula V:

Formula V

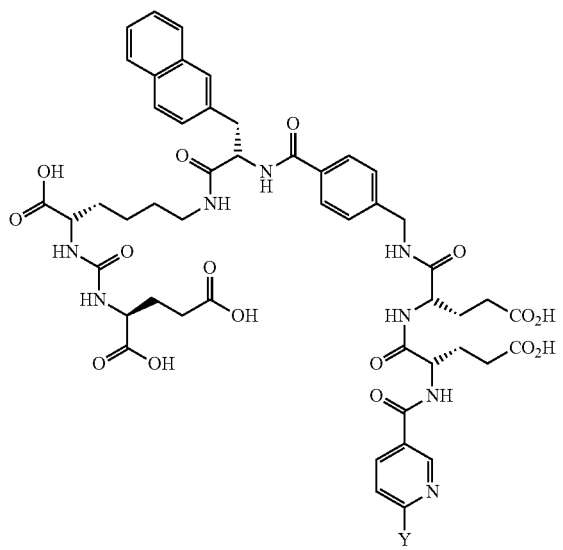

wherein substituent Y is selected from the group consisting of —N$^+$(R$^1$R$^2$R$^3$), —NO$_2$, —Cl, —Br, —F, or —I, and R$^1$, R$^2$, and R$^3$ are the same or different from each other and each are unsubstituted or substituted $C_1$-$C_6$ alkyl. The bonding unit of the precursor shown in formula V corresponds to the bonding unit shown in formula I, wherein m and n each are 1.

A precursor that is more preferred for the preparation of [$^{18}$F]F-PSMA-1007 is a compound of general formula Va:

Formula Va

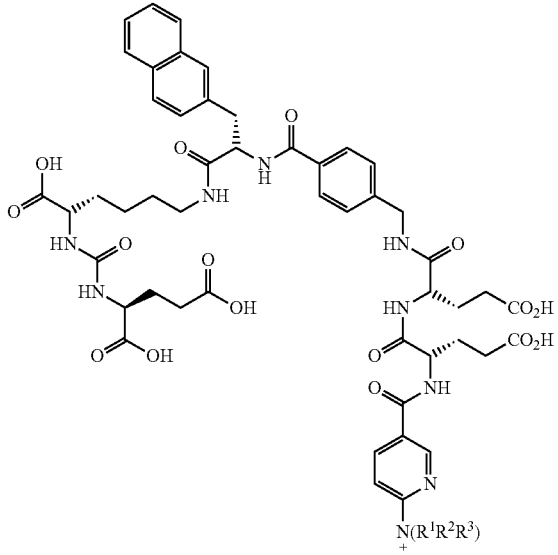

wherein $R^1$, $R^2$, and $R^3$ are the same or different from each other and each are unsubstituted or substituted $C_1$-$C_6$ alkyl. Particularly preferred, $R^1$, $R^2$, and $R^3$ each are methyl. A precursor of formula Va, in which $R^1$, $R^2$, and $R^3$ each are methyl, is illustrated in formula Vb.

Formula Vb

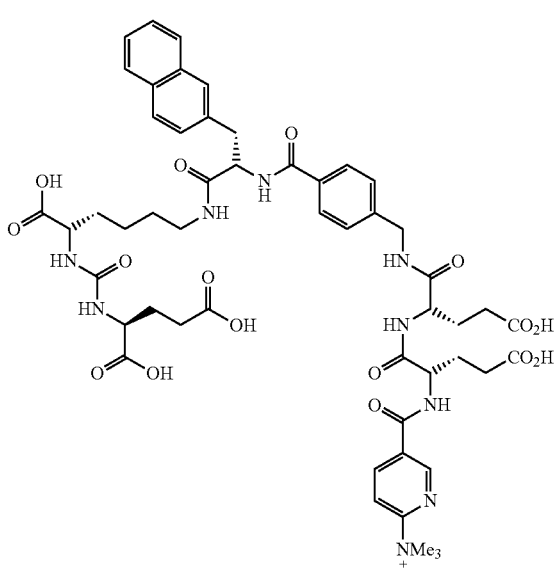

Preferably, the precursor is provided in a aprotic, polar solvent such as acetonitrile, dimethylformamide (DMF), N,N-dimethylacetamide (DMAA), N-methyl-2-pyrrolidone (NMP), dimethylsulfoxide (DMSO) or mixtures thereof.

The [$^{18}$F] fluoride anion used in step (b) can be prepared by means of known methods. For example, the [$^{18}$F] fluoride anion is prepared in the cyclotron by irradiating H$_2^{18}$O enriched to at least 97% with protons of an energy of 9.6 MeV. The so obtained aqueous [$^{18}$F] fluoride solution is fixed on an anion exchange cartridge (QMA) and transferred into a reaction vessel by means of a phase transfer catalyst (PTC), such as crown ethers, quaternary ammonium salts, or alkali or alkaline-earth salts. As the PTC it is preferably made use of a [2,2,2]-cryptand (Kryptofix® or K222), tetra-n-butyl-ammonium phosphate, hydroxide, oxalate, toluenesulphonate, or optionally other crown ethers, such as 18-crown-6. After an azeotropic dehydration the precursor is dissolved in an organic solvent and added to the dried reaction mixture. The organic solvent may be an aprotic, polar solvent such as acetonitrile, dimethylformamide (DMF), N,N-dimethylacetamide (DMAA), N-methyl-2-pyrrolidone (NMP), dimethylsulfoxide (DMSO), or mixtures thereof. Preferably, dimethylsulfoxide is used as the solvent.

Step (b) is preferably carried out under a thermal reaction regime in the closed reaction vessel at an elevated temperature. Step (b) of the method according to the invention is preferably carried out in an aprotic, polar solvent, such as acetonitrile, dimethylformamide (DMF), dimethylsulfoxide (DMSO), or mixtures thereof. Preferably, dimethylsulfoxide is used as the solvent. Preferably, the method is carried out at a pH value of 1 to 8. Preferably, the pH value is in the range of 4 to 8, particularly preferred at 5. However, the method can also be carried out at a pH value above 8, where however lower yields are achieved. The inventors have surprisingly found that just at a pH value in the range of from 4 to 8 less by-compounds are generated and an extremely high labeling yield can be achieved.

Step (b) of the method according to the invention is preferably carried out for a time period of from 1 to 60 min, more preferably from 3 to 30 min, and particularly preferred from 8 to 20 min.

Step (b) of the method according to the invention is preferably carried out at temperatures below 100° C., more preferably at temperatures between room temperature and 95° C., even more preferably between room temperature and 90° C., and particularly preferred at temperatures between 70 and 90° C.

Step (b) of the method according to the invention may also be carried out as a microwave-assisted reaction. For that, microwaves of a wattage of 50 to 150 W, preferably 75 to 85 W are radiated onto a specific closed reaction vessel.

To determine the labeling yield and radioactive by-products thin-layer chromatography (TLC) and high performance liquid chromatography (HPLC) can be used.

Scheme 3 illustrates a preferred embodiment of the method according to the invention. Here, a precursor of formula IV is reacted to [$^{18}$F]-DCFPyL in the presence of [$^{18}$F] fluoride anions and an activation salt:

Scheme 3

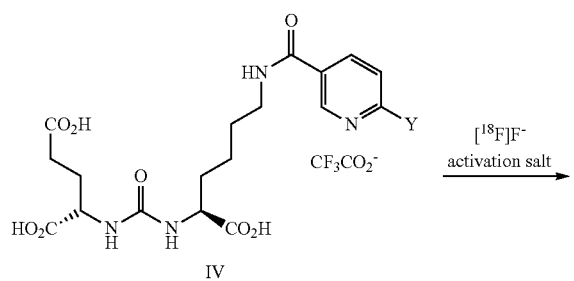

IV

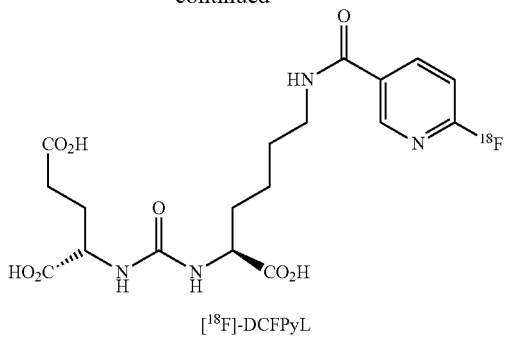

[$^{18}$F]-DCFPyL

It should be noted that the precursor can have another anion instead of the CF$_3$COO$^-$ anion. Preferably, the activation salt is TBA, particularly preferred TBA phosphate.

Scheme 3a illustrates a preferred embodiment of the method according to the invention. Here, a precursor of formula IVa is reacted to [$^{18}$F]-DCFPyL in the presence of [$^{18}$F] fluoride anions and an activation salt:

Scheme 3a

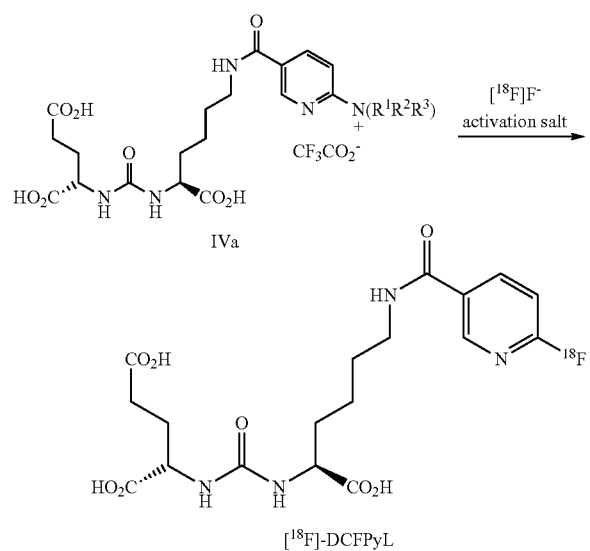

[$^{18}$F]-DCFPyL

It should be noted that the precursor can have another anion instead of the CF$_3$COO$^-$ anion. Preferably, the activation salt is TBA, particularly preferred TBA phosphate.

In a preferred embodiment a precursor of formula IVb for the preparation of [$^{18}$F]-DCFPyL in the presence of [$^{18}$F] fluorine anions and TBA, preferably TBA phosphate, as an activation salt is reacted, as is shown in scheme 3b.

Scheme 3b

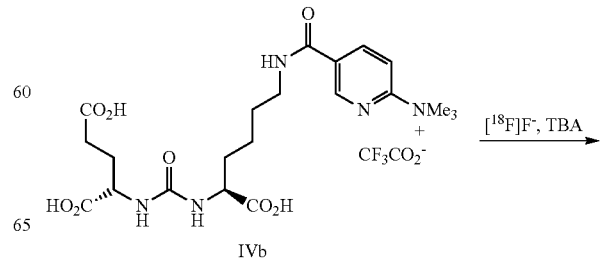

IVb

15
-continued
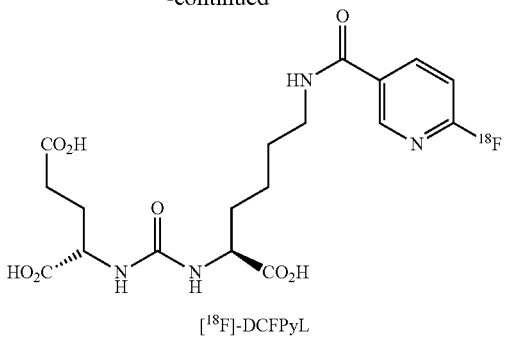
[18F]-DCFPyL
16
It should be noted that the precursor can have another anion instead of the CF₃COO⁻ anion.
Scheme 4 illustrates a preferred embodiment of the method according to the invention. Here, a precursor of formula V is reacted to [¹⁸F]F-PSMA-1007 in the presence of [¹⁸F] fluoride anions and an activation salt:
Scheme 4
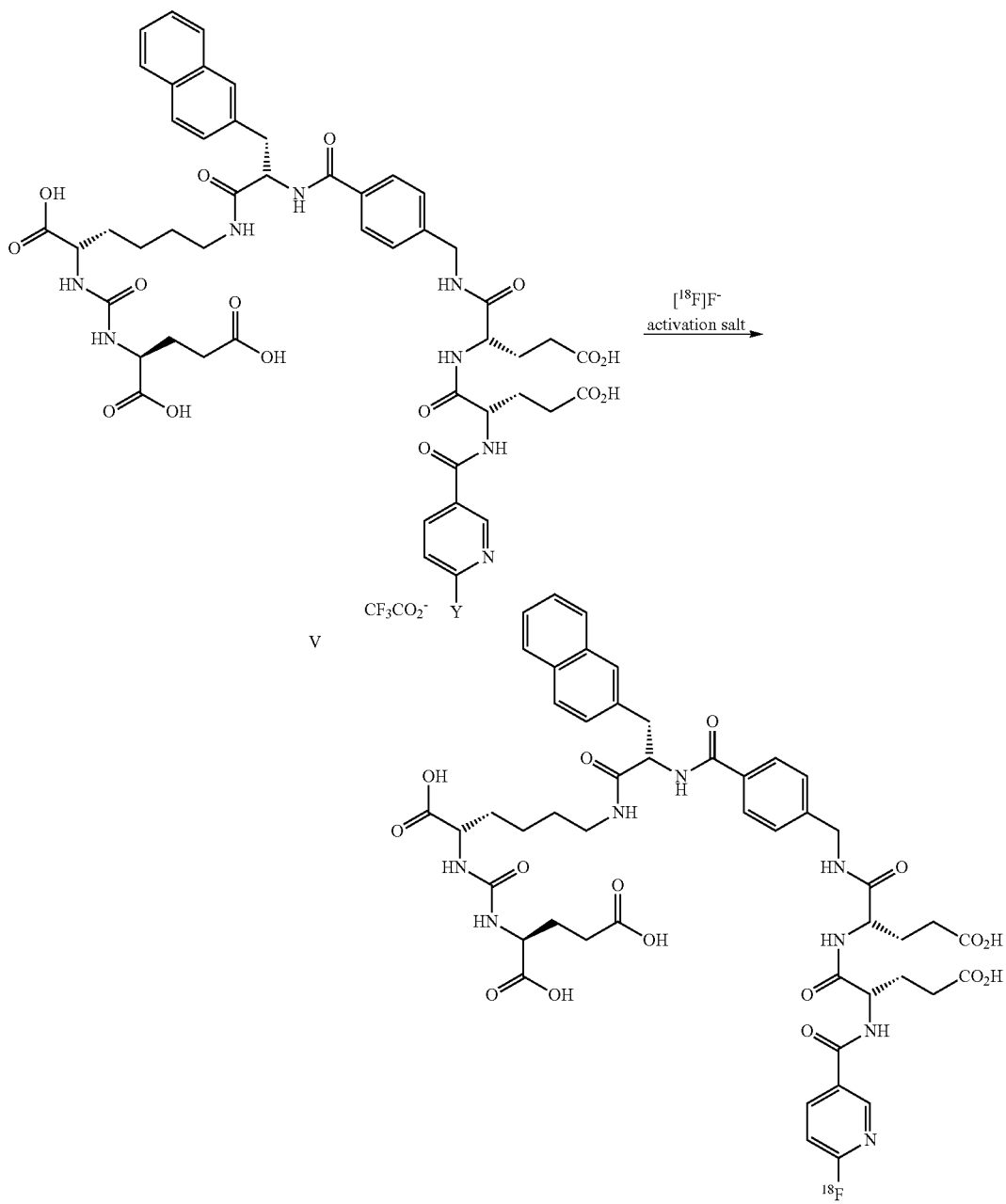
[18F]F-PSMA-1007

It should be noted that the precursor can have another anion instead of the $CF_3COO^-$ anion. Preferably, the activation salt is TBA, particularly preferred TBA phosphate.

Scheme 4a illustrates a preferred embodiment of the method according to the invention. Here, a precursor of formula Va is reacted to [$^{18}$F]F-PSMA-1007 in the presence of [$^{18}$F] fluoride anions and an activation salt:

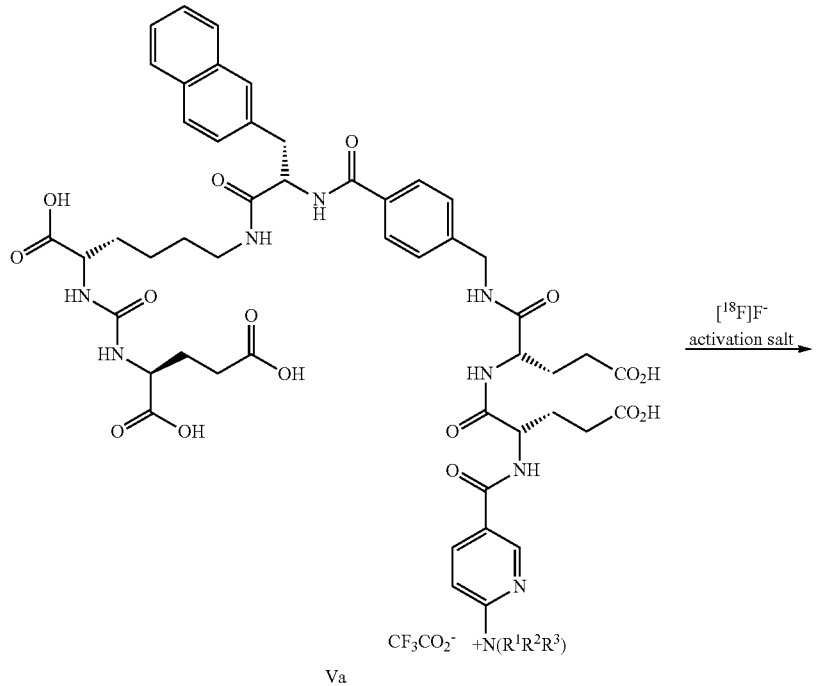

It should be noted that the precursor can have another anion instead of the CF₃COO⁻ anion. Preferably, the activation salt is TBA, particularly preferred TBA phosphate.

In a particularly preferred embodiment a precursor of formula Vb for the preparation of [$^{18}$F]F-PSMA-1007 in the presence of [$^{18}$F] fluorine anions and TBA, preferably TBA phosphate, as an activation salt is reacted, as is shown in scheme 4b.

It should be noted that the precursor can have another anion instead of the CF₃COO⁻ anion.

According to the invention, further a precursor for the preparation of a radiofluorinated compound is provided. The precursor has an aromatic or heteroaromatic ring, which carries a substituent Y, a bonding unit, which can bind to a peptide or peptide mimetic, as well as a spacer group, which connects the aromatic or heteroaromatic ring to the bonding Scheme 4b

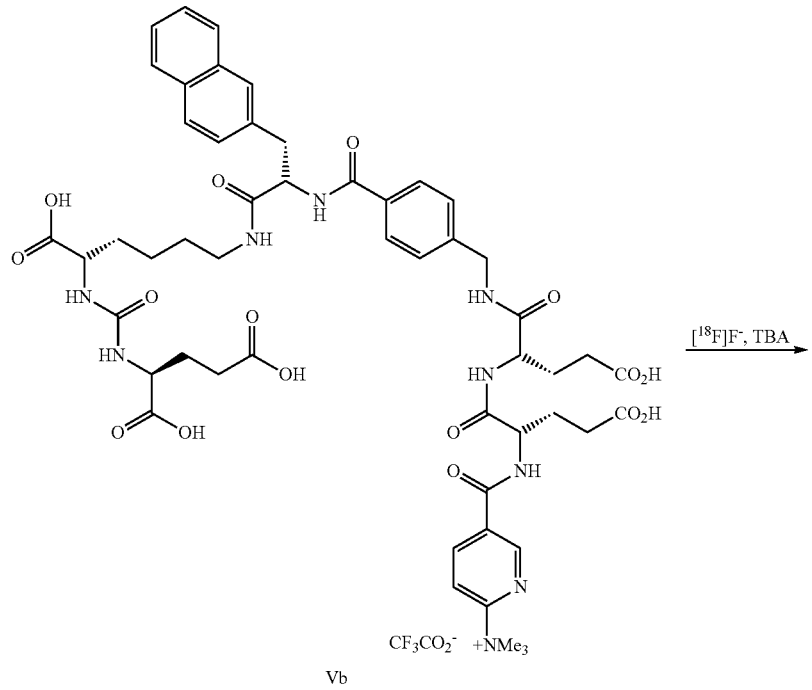

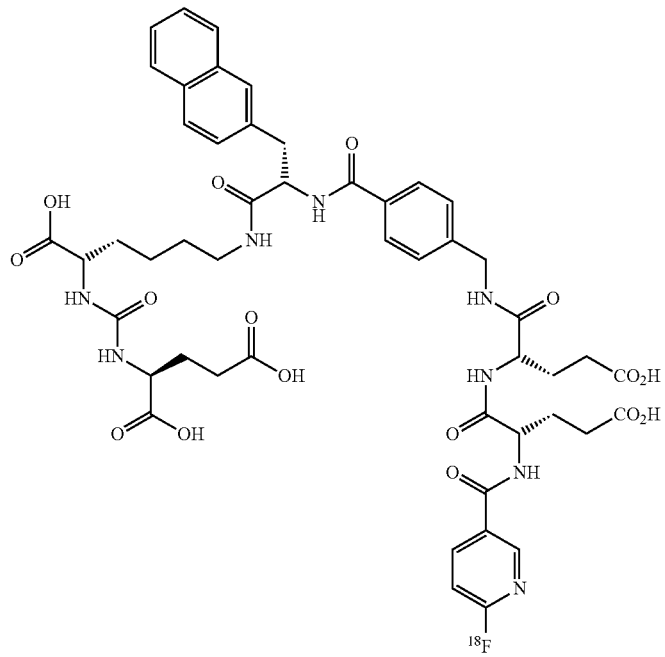

[18F]F-PSMA-1007 unit. The bonding unit carries at least one second substituent selected from the group consisting of —OH, —CONH, and —COOH, wherein the bonding unit is connected to the spacer group via a bond $A^1$ and the spacer group is connected to the aromatic or heteroaromatic ring via a bond $A^2$. Here, substituent Y is selected from the group consisting of —$N^+(R^1R^2R^3)$, —$NO_2$, —Cl, —Br, —F, or —I, $R^1$, $R^2$, and $R^3$ are the same or different from each other and each are unsubstituted or substituted $C_1$-$C_6$ alkyl. Further details on the precursor according to the invention have been described above in context with the method according to the invention.

According to the invention, further there is provided the use of the precursor according to the invention for the preparation of a radiofluorinated compound, which has an aromatic or heteroaromatic ring, which carries the [$^{18}$F] fluorine as the first substituent, a bonding unit, which can bind to a peptide or a peptide mimetic, as well as a spacer group, which connects the aromatic or heteroaromatic ring to the bonding unit. The bonding unit can carry at least one second substituent selected from the group consisting of —OH, —CONH, and —COOH, wherein the bonding unit is connected to the spacer group via a bond $A^1$ and the spacer group is connected to the aromatic or heteroaromatic ring via a bond $A^2$.

The invention allows a one-stage synthesis of the shown radiofluorinated compounds. On the one hand, this shortens the synthesis time. On the other hand, the labeling yields achieved can be more than twice as high as with the two-stage process known in the literature. Moreover, the reaction product of a one-stage synthesis is easier to purify, by which it can be refrained from HPLC that is costly in terms of equipment. The radiofluorinated compounds can be purified very easily and less time-consuming with cartridges, so-called SPE cartridges. Further, it is preferred to avoid concentrated acids and bases in the GMP environment (GMP=good manufacturing practice), since in GMP fields often corrodible stainless steel has been used. The simplicity of the method according to the invention allows an automated synthesis of the radiofluorinated compound according to the invention, for example by means of a disposable cassette and a reagent kit on a common synthesis module. Purification can be carried out during the synthesis by means of the SPE cartridge, so that at the end of the synthesis a ready-to-use solution of the radiofluorinated compound according to the invention can be provided.

The precursor according to the invention carries the at least one second substituent, i.e. at least one unprotected OH, CONH and/or COOH group, which is also carried by the target compound, i.e. the radiofluorinated compound. It was not to be expected that radioactive labelings at compounds carrying unprotected OH, CONH, and COOH groups do work. With the present invention in practice a significant simplification of the automated synthesis and thus, the preparation of the radiofluorinated compound can be achieved, since the synthesis in at least two stages, as before, is no longer needed, but can be done in one stage with significant time saving. Time saving allows a significantly increased yield and thus, an easier and higher availability of the radiofluorinated compound. Therefore, more activity is gained from a radiosynthesis, and thus, when using the radiofluorinated compound prepared in the radiosynthesis as a radiotracer, more patients can be examined.

The invention is explained in detail with the help of examples that are not intended to limit the invention.

EXAMPLE 1

Synthesis of a Precursor of Formula IVb

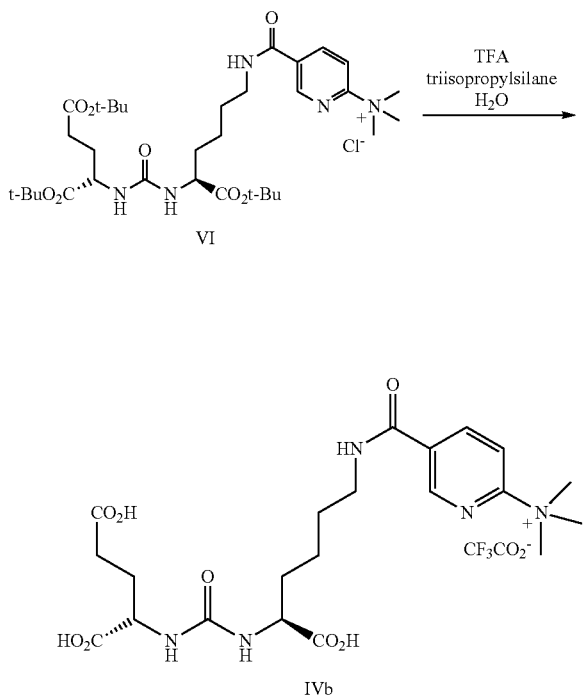

Synthesis of the starting compound VI is as described in literature (Ravert et al., *J. Label Compd. Radiopharm* 2016, 59, 439-50; Bouvet et al., EJNMMMI Research, 2016, 6: 40). In a mixture of 23.5 ml of trifluoroacetic acid, 0.62 ml of triisopropylsilane, and 0.62 ml of water 2.48 g of the starting compound XX were dissolved and stirred for 3 h at room temperature. Subsequently, the reaction mixture was dropwise added to 241 ml of MTB ether under cooling with an ice bath and vigorously stirring. The precipitated white solid was sucked off by a frit and washed two times with 100 ml of MTB ether. 1.82 g (84%) of the precursor of formula IVb (=5-((S)-5-carboxy-5-(3-((S)-1,3-dicarboxy-propyl) ureido)pentyl-carbamoyl)-N,N,N-trimethylpyridine-2-aminium-2,2,2-trifluoro-acetate) were separated as a white solid.

EXAMPLE 2

Synthesis of a Precursor of Formula Vb

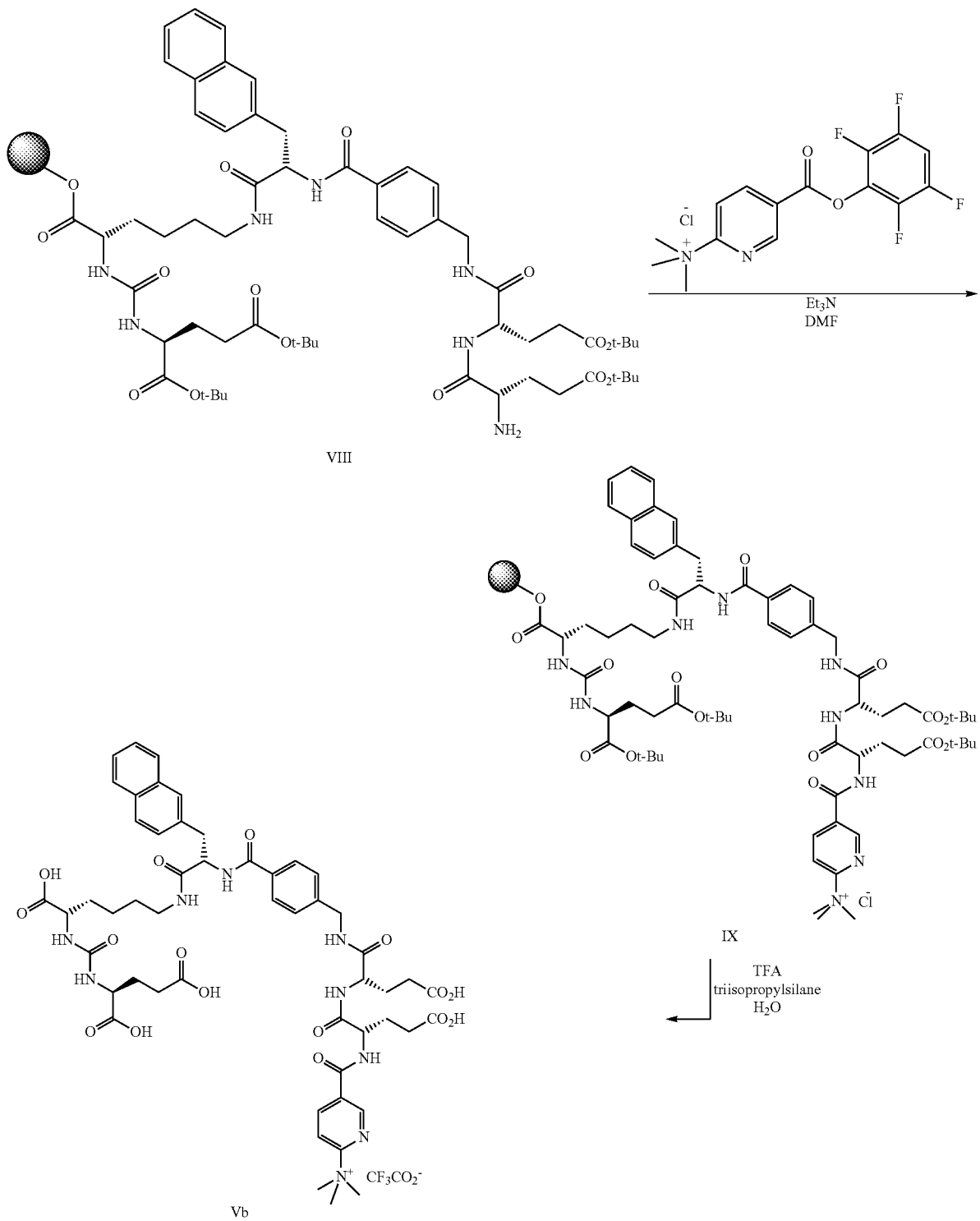

The synthesis of the starting compound VIII is as described in literature (Cardinale et al., J. Nucl. Med. 2016, accepted for publication; WO 2015/062370 A1). 0.2 mmol of the starting compound VIII were shaken in 3.5 ml of dimethylformamide for 30 min. Thereafter, 109 mg of N,N,N-trimethyl-5-((2,3,5,6-tetrafluorophenoxy)-carbonyl) pyridine-2-aminiumchloride (Olberg et al., *J. Med. Chem.* 2010, 53, 1732-1740) and 0.042 ml of triethylamine were added. The reaction mixture was shaken for 2 h, before the resin was filtered and washed three times with DMF and three times with dichloromethane. For cleavage and deprotection, the resin was shaken with a mixture of 4 ml of trifluoroacetic acid, 0.11 ml of triisopropylsilane, and 0.11 ml of water for 90 min. Subsequently, the mixture was filtered, and the filtrate was added dropwise to 40 ml of MTB ether. The mixture was centrifuged, the supernatant solution was pipetted off, and the residue was washed three times with MTB ether. Purification was by HPLC. 172 mg (72%) of the precursor of formula Vb (=5-((S)-4-carboxy-1-((S)-4-carboxy-1-(4-((S)-1-((S)-5-carboxy-5-(3-((S)-1,3-dicarboxy-propyl)-ureido)pentylamino)-3-(naphthalene-2-yl)-1-oxopropane-2-ylcarbamoyl)-benzylamino)-1-oxobutane-2-ylamino)-1-oxobutane-2-ylcarbamoyl)-N,N,N-trimethylpyridine-2-aminium-2,2,2-trifluoroacetate) were separated as a white solid.

EXAMPLE 3

Reaction of a Precursor of Formula IVb in the Presence of Tetra-n-Butyl-Ammonium-Hydrogen Carbonate to [$^{18}$F]-DCFPyL A reaction mixture of 7.5 mg of a precursor of formula IVb in 1 ml of DMF, 1 ml of 0.075M tetra-n-butyl-ammonium hydrogen carbonate (TBA-HCO$_3$) and [$^{18}$F] fluoride anions was reacted at a pH value of about 8.5 for 14 min at 75° C. 47.9% of [$^{18}$F]-DCFPyL were obtained. Additionally, radioactive by-compounds could be detected. The proportion of [$^{18}$F] fluoride was 28.6%.

EXAMPLE 4

Reaction of a Precursor of Formula IVb in the Presence of Tetra-n-Butyl-Ammonium Toluene Sulphonate to [$^{18}$F]-DCFPyL A reaction mixture of 7.5 mg of a precursor of formula IVb in 1 ml of DMF, 750p of 0.075M tetra-n-butyl-ammonium toluene sulphonate (TBA toluene sulphonate), and [$^{18}$F] fluoride anions was reacted at a pH value of about 5.0 for 14 min at 75° C. 37.4% of [$^{18}$F]-DCFPyL and 30.9% of [$^{18}$F] fluoride were detected. Additionally, radioactive by-compounds were detected the proportion of which was approx. 30%.

EXAMPLE 5

Reaction of a Precursor of Formula IVb in the Presence of Tetra-n-Butyl-Ammonium Phosphate to [$^{18}$F]-DCFPyL A reaction mixture of 2.5 mg of a precursor of formula IVb in 1.5 ml of DMF, 750 µl of 0.075M tetra-n-butyl-ammonium phosphate (TBA phosphate) and [$^{18}$F] fluoride anions was reacted at a pH value of about 4.7 for 10 min at 85° C. Under these conditions, the precursor was almost quantitatively converted to [$^{18}$F]-DCFPyL (97.0%). The by-compounds could be reduced to less than 2%, residual [$^{18}$F] fluoride could only be detected in traces.

EXAMPLE 6

Reaction of a Precursor of Formula IVb in the Presence of Tetra-n-Butyl-Ammonium Hydrogen Sulphate to [$^{18}$F]-DCFPyL A reaction mixture of 7.5 mg of a precursor of formula IVb in 1 ml of DMF, 750 µl of 0.075M tetra-n-butyl-ammonium hydrogen sulphate (TBA hydrogen sulphate) and [$^{18}$F] fluoride anions was reacted at a pH value of about 1.7 for 14 min at 75° C. 15.6% of [$^{18}$F]-DCFPyL were obtained, whereas the proportion of [$^{18}$F] fluoride was 73.4%. Thus, labeling with [$^{18}$F]fluoride anions was relatively poor.

Examples 3 to 6 show that the reaction of precursors of formula IVb with [$^{18}$F] fluoride anions in the presence of TBA as an activation salt in a one-stage method results in relatively high yields of the radiofluorinated compound [$^{18}$F]-DCFPyL. Example 5 shows that in the slightly acidic pH range with TBA phosphate only traces of the by-compounds are generated and an extremely high labeling yield can be achieved.

EXAMPLE 7

Reaction of a Precursor of Formula Vb in the Presence of Tetra-n-Butyl-Ammonium Hydrogen Carbonate to [$^{18}$F]-PSMA-1007

A reaction mixture of 10 mg of a precursor of formula Vb in a mixture of 1 ml of acetonitrile and 600 µl of DMF, 750 µl of 0.075M TBA hydrogen carbonate, and [$^{18}$F] fluoride anions was incubated at a pH value of approx. 7 for 10 min at 120° C. In addition to 37.9% of free [$^{18}$F]fluoride, 59.3% of [$^{18}$F]F-PSMA-1007 were detected. A radioactive by-product could be detected in traces.

EXAMPLE 8

Reaction of a Precursor of Formula Vb in the Presence of Tetra-n-Butyl-Ammonium Hydrogen Carbonate to [$^{18}$F]-PSMA-1007

A reaction mixture of 2.5 mg of a precursor of formula Vb in 1.5 ml of DMF, 750 µl of 0.075M TBA hydrogen carbonate, and [$^{18}$F] fluoride anions was incubated at a pH value of approx. 7 for 10 min at 85° C. In addition to 8.2% of free [$^{18}$F] fluoride, 90.7% of [$^{18}$F]-PSMA-1007 were detected. A radioactive by-product could be detected in traces.

EXAMPLE 9

Reaction of a Precursor of Formula Vb in the Presence of Tetra-n-Butyl-Ammonium Phosphate to [$^{18}$F]-PSMA-1007

A reaction mixture of 2.5 mg of a precursor of formula Vb in 1.5 ml of DMF, 750 µl of 0.075M TBA phosphate, and [$^{18}$F] fluoride anions was incubated at a pH value of approx. 4.7 for 10 min at 85° C. The desired product [$^{18}$F]-PSMA-1007 was quantitatively formed (99.6%). Free [$^{18}$F] fluoride could only be detected in traces.

Examples 7 to 9 show that the reaction of precursors of formula Vb with [$^{18}$F] fluoride anions in the presence of TBA as an activation salt in a one-stage method results in relatively high yields of the radiofluorinated compound [$^{18}$F]-PSMA-1007. Example 9 shows that in the slightly acidic pH range with TBA phosphate a quantitative labeling yield can be achieved.

EXAMPLE 10

Fully Automated Reaction of a Precursor of Formula Vb in the Presence of Tetra-n-Butyl-Ammonium Hydrogen Carbonate to [$^{18}$F]-PSMA-1007 by Means of a Synthesis Module GE TRACERlab® MX$_{FDG}$ With solvent-resistant stopcocks a cassette for the synthesis of [$^{18}$F]-PSMA-1007 was established in analogy to a FDG synthesis cassette on a GE TRACERlab® MX$_{FDG}$ and a synthesis sequence was developed. In detail, the synthesis proceeds in accordance with the following steps: concentrating the [$^{18}$F] fluoride on a QMA cartridge, elution with 0.750 ml of TBA hydrogen carbonate, and subsequently drying at 95° C. for 15 min, radioactive labeling with 3 mg of a precursor of formula Vb in 2 ml of DMF for 14 min at 85° C., SPE purification and reformulation. [$^{18}$F]-PSMA-1007 could be obtained in radiochemical yields >40%. The radiochemical purity was >95%.

The invention claimed is:

1. A method for producing a radiofluorinated compound, which has an aromatic or heteroaromatic ring, which carries [$^{18}$F] fluorine as a first substituent, a bonding unit, which can bind to a peptide and a spacer group, which connects the aromatic or heteroaromatic ring to the bonding unit, wherein the aromatic or heteroaromatic ring carries [$^{18}$F] fluorine as the first substituent, wherein the bonding unit carries at least one second substituent selected from the group consisting of —OH, —CONH, and —COOH, wherein the bonding unit is connected to the spacer group via a bond A$^1$ and the spacer group is connected to the aromatic or heteroaromatic ring via a bond A$^2$, wherein:

the bonding unit is a bonding unit of general formula I:

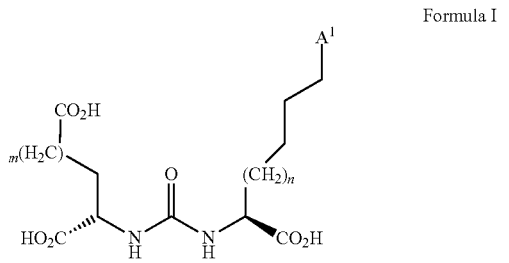

Formula I wherein A$^1$ is the bond via which the bonding unit is connected to the spacer group, m and n are the same or different from each other and each are an integer of from 0 to 10;

the spacer group is a spacer group of general formula II or general formula III:

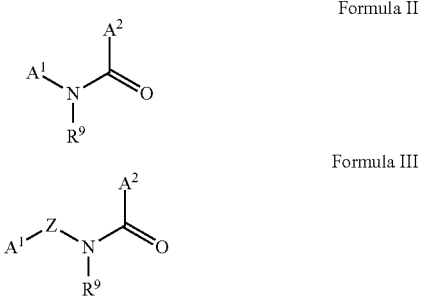

Formula II

Formula III wherein A$^1$ is the bond via which the spacer group is connected to the bonding unit, A$^2$ is the bond via which the spacer group is connected to the aromatic or heteroaromatic ring of the precursor or to the radiofluorinated compound, R$^9$ is hydrogen or an unsubstituted or substituted C$_1$-C$_6$ alkyl group, and Z is an unsubstituted or mono- or poly-substituted hydrocarbon; and the method comprises the steps of:

(a) providing a precursor, which has the aromatic or heteroaromatic ring, which carries a substituent Y, the bonding unit, which can bind to the peptide and which carries at least one second substituent selected from the group consisting of —OH, —CONH, and —COOH, as well as the spacer group, wherein the aromatic or heteroaromatic ring, which carries a substituent Y, is of general formula VId

Formula VId wherein

X each is C—R$^8$ or N, with the provision that at most two of moieties X are N and the remaining of moieties X are C—R$^8$ and R$^8$ each independently is the bond A$^2$ to the spacer, hydrogen, or unsubstituted or substituted C$_1$-C$_6$ alkyl, with the provision that exactly one residue R$^8$ is a bond A$^2$ to the spacer group and the remaining ones of R$^8$ are the same or different from each other and each represent hydrogen or unsubstituted or substituted C$_1$-C$_6$ alkyl; and substituent Y is selected from the group consisting of —N$^+$(R$^1$R$^2$R$^3$), —NO$_2$, —Cl, —Br, —F, or —I, and R$^1$, R$^2$, and R$^3$ are the same or different from each other and each are unsubstituted or substituted C$_1$-C$_6$ alkyl, wherein the precursor only differs from the radiofluorinated compound in that substituent Y is replaced by [$^{18}$F]fluorine; and (b) reacting the precursor with a [$^{18}$F] fluoride anion in the presence of an activation salt to the radiofluorinated compound in a one-stage synthesis, wherein substituent Y is replaced by [$^{18}$F]fluoride and wherein the activation salt has a cation of general formula N$^+$(R$^4$R$^5$R$^6$R$^7$), wherein R$^4$, R$^5$, R$^6$, and R$^7$ are the same or different from each other and each are unsubstituted or substituted C$_1$-C$_6$ alkyl.

2. The method according to claim 1, wherein R$^1$, R$^2$, and R$^3$ each are methyl.

3. The method according to claim 1, wherein R$^4$, R$^5$, R$^6$, and R$^7$ each are n-butyl.

4. The method according to claim 1, wherein the activation salt has an anion selected from the group comprising hydrogen carbonate, hydrogen sulphate, oxalate, phosphate, and toluenesulphonate.

5. The method according to claim 1, wherein the activation salt is tetra-n-butyl-ammonium hydrogen carbonate.

6. The method according to claim 1, wherein Z is a group of formula VII:

Formula VII
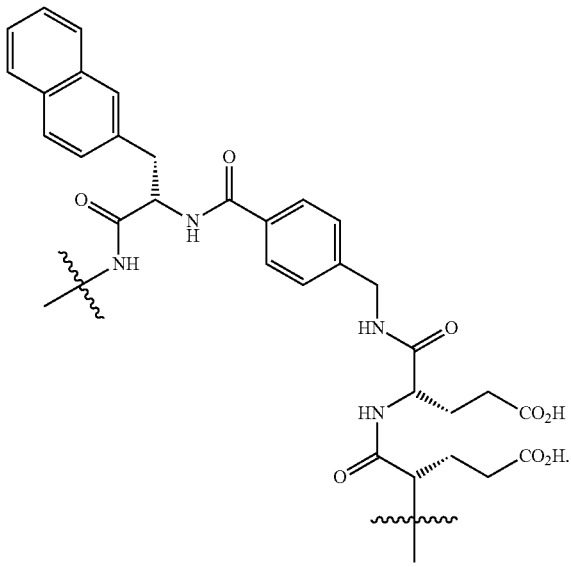
7. The method according to claim 1, wherein the precursor is a compound of formula IVa:
Formula IVa
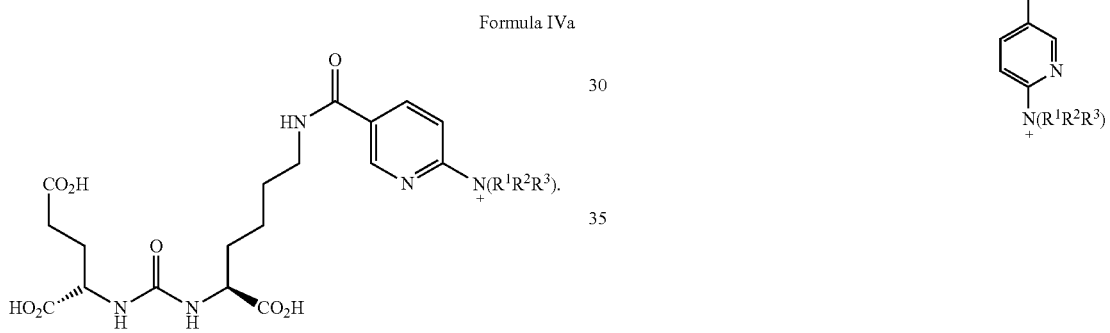
8. The method according to claim 6, wherein the precursor is a compound of formula Va:
Formula Va
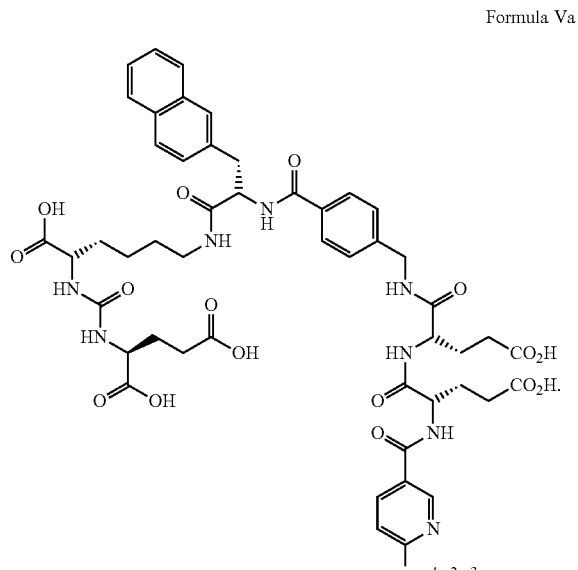
* * * * *